(12) United States Patent
Lurye

(10) Patent No.: US 11,083,779 B2
(45) Date of Patent: Aug. 10, 2021

(54) METHOD FOR TREATMENT OF ENCEPHALOPATHY

(71) Applicant: Arman Lurye, Almaty (KZ)

(72) Inventor: Arman Lurye, Almaty (KZ)

(*) Notice: Subject to any disclaimer, the term of this patent is extended or adjusted under 35 U.S.C. 154(b) by 204 days.

(21) Appl. No.: 16/116,821

(22) Filed: Aug. 29, 2018

(65) Prior Publication Data

US 2019/0275114 A1 Sep. 12, 2019

(30) Foreign Application Priority Data

Mar. 6, 2018 (KZ) ................. 2018/0146.1

(51) Int. Cl.
| | |
|---|---|
| *A61K 38/26* | (2006.01) |
| *A61K 38/28* | (2006.01) |
| *A61K 9/00* | (2006.01) |
| *A61K 45/06* | (2006.01) |
| *A61K 38/16* | (2006.01) |
| *A61P 43/00* | (2006.01) |
| *A61K 38/17* | (2006.01) |

(52) U.S. Cl.
CPC ............ *A61K 38/28* (2013.01); *A61K 9/0019* (2013.01); *A61K 38/168* (2013.01); *A61K 38/1709* (2013.01); *A61K 45/06* (2013.01); *A61P 43/00* (2018.01)

(58) Field of Classification Search
CPC ................................ A61K 38/26; A61K 38/28
See application file for complete search history.

(56) References Cited

PUBLICATIONS

Candeias et al., World J. Diabetes 25, 807-827, 2015.*

* cited by examiner

*Primary Examiner* — Gyan Chandra
(74) *Attorney, Agent, or Firm* — The Roy Gross Law Firm, LLC; Roy Gross

(57) ABSTRACT

A method of treatment of encephalopathy, the method comprising decreasing concentration of glucose in a patient's blood stream to 1.6-3.6 mmol per liter by intravenous insulin administrating and consecutively administering the patient with single doses of a plurality of pharmacological solutions with a 30-second interval, wherein, first pharmacological solution administered to the patient is a pharmacological solution comprising a vascular medicine with pharmacological effect, wherein second pharmacological solution administered to the patient is a straight nootropic effected pharmacological composition, wherein third pharmacological solution administered to the patient is a peptide pharmacological composition, and wherein fourth pharmacological solution administered to the patient is a metabolic pharmacological composition.

15 Claims, No Drawings

METHOD FOR TREATMENT OF ENCEPHALOPATHY

PRIORITY CLAIM

The present application claims priority to a Republic of Kazakhstan Patent Application No. 2018/0146.1, filed on Mar. 6, 2018, which is incorporated herein by reference.

FIELD

The present invention relates to the treatment of organic disease of encephalopathy by means of structured injection of a pharmacological composition having enhanced characteristics.

BACKGROUND

Encephalopathy is the common identification of non-inflammatory cerebral diseases. Encephalopathy can be inborn and acquired (organic affections of brain connected with intoxications, infections, alcoholism, traumas, hypovitaminosis, vascular diseases of brain, lack of vitamin B1, and the like). Manifestations may be classified into pseudoneurotic and psychopathy-like. Treatment of encephalopathy depends on cause that evoked it. The present disclosure is directed to the treatment of patients with encephalopathy of vascular, traumatic, inflammatory and other genesis.

There are several known several ways of treatment of chronic neurological diseases. Namely, toxic encephalopathy, including administering of the pharmacological composition PIRACETAM® in combination with a physiotherapy in the form of a transcranial electrical stimulation of a brain.

At the same time, PIRACETAM® is intravenously administered to the patient in 10-15 minutes before the beginning of a transcranial electrical stimulation of a brain which is carried out in two steps, each lasting 15-20 minutes. First stage at an average frequency of 77 Hz, the second stage at an average frequency of 10 Hz. (Russian Federation Patent No. RU2362596, C. A61N1/00, A61P25/00, pub. 27 Jul. 2009). In this case of treatment patients are observing the decrease of headaches, giddiness and the improvement of sleep.

Also is known a method of treating vascular encephalopathy by complex medical therapy, wherein the administering to a patient using vinpocetine, RIBOXINE® riboxine, vitamin B6, and ceruloplasmin, where ceruloplasmin is administered daily for 8-10 days intravenously at a rate of 30-35 drops per minute at a dose of 100-200 mg in the form of a solution containing 200 ml of isotonic sodium chloride solution per 100 mg of ceruloplasmin (Russian Federation Patent No. RU 2242989, cl. A61K 38/00, A61P 9/10, pub. 20 Aug. 2004). According to the authors, the method provides an increase in the number of patients with an improvement in the physical state and the achievement of a higher degree of reduction in headaches.

However, the known methods of treatment of encephalopathy do not appear to be insufficiently effective as there is no mentioning of patients' speech recovery, restoration of sensitivity and mobility of extremities, processes of retaining and recalling data, and improvement of a mood of patients.

The objective of the disclosed invention is development of more efficient ways of treatment of encephalopathy, with ensuring lasting clinical effect by increasing nootropic, vasoactive and neurotrophic efficiency of the administered medicamental drugs.

DETAILED DESCRIPTION

In the preferred embodiment of the present disclosure, the disclosed method is implemented by reducing the level of glucose in the blood until 1.6-3.6 mmol/1, by administering insulin. The second step in the preferred embodiment, an enhanced pharmacological vascular composition (with pharmacological effect) is sequentially injected in single doses, in the 30-second interval, along with pharmacological solution having a direct nootropic action, pharmacological solution of peptide medicine and pharmacological solution of metabolic medicine. Procedures of administering of the aforementioned pharmacological compositions are carried out once a week, generally, in total of four administering sessions.

As may be appreciated by the person skilled in the art, pharmacological compositions of CAVINTON® ($C_{22}H_{26}N_2O_2$), VINPOCETINE® ($C_{22}H_{26}N_2O_2$), TRENTAL® ($C_{13}H_{18}N_4O_3$), or PENTOXIFYLLINE® ($C_{13}H_{18}N_4O_3$) are used as a vascular composition with pharmacological composition with pharmacological effect. Also, pharmacological compositions of PIRACETAM® ($C_6H_{10}N_2O_2$) or NOOTROPIL® ($C_6H_{10}N_2O_2$) or MEXIDOL® ($C_8H_{11}NO$) or CERAXON® ($C_{14}H_{27}N_4O_{11}P_2+$) are used as pharmacological composition having a direct nootropic action. Furthermore, pharmacological compositions of CORTEXIN® or CEREBROLYSIN® as used as peptide drugs. Finally, pharmacological compositions of ACTOVEGIN® or solcoseryl are administered as metabolic compositions.

Using small doses of insulin for creation of a short-term insignificant hypoglycemia before the maintenance of a glucose in a blood of the patient of 1.6-3.6 mmol/1 by intravenous administration of an insulin and, entering intravenously, consistently, with an interval of 1 minute, solutions of VINPOCETINE®, PIRACETAM®, CORTEXIN® and ACTOVEGIN® it was succeeded to reach appreciable positive dynamics at patients with different types of encephalopathy. During lowering of level of glucose in a blood and simultaneous administration of medicines the metabolic activity of a brain changes that is shown by essential positive changes at patients after therapy.

After four pharmacological administering sessions, the appreciable positive effect which is shown in stopping of symptoms of encephalopathy, as recovery of the speech, restoration of sensitivity and mobility of limbs, exception of giddiness, headaches, ease of processes of storing and procreation of information, decrease of nervousness and concern. The specified significant improvement of the condition of health providing improvement of quality of life to many patients (according to age), allowed to return to work. The above-described effect of the disclosed method of treatment has proven to have a long-lasting effect, which is confirmed by the close clinical observation of subject patients in the course of over five years.

It is well-known that insulin is administered during the coma therapy for an intensive care of psychoses, for example, of acute schizophrenic psychosis (A.I. Nelson "A short guide for doctors on use of a method of insulin coma therapy", 2004), where patients, by using insulin, are entered into coma in the conditions of psychoreanimotology.

It is also well-known that symptoms of a hypoglycemia are knowingly used in a way of the treatment of malignant tumors including a chemotherapy according to which insulin is injected in a short action in a dose of 8-10 IU and at achievement of symptoms of a hypoglycemia intravenously are entered chemotherapy drugs along with 40% solution of a glucose in volume 200-250 ml (Russian Federation Patent No. RU2272647). However, insulin has never been administered for the purposes of treatment of encephalopathy.

In the preferred embodiment of the disclosed invention, of the method of treatment of encephalopathy is carried out as follows.

The method is carried out on a patient's empty stomach, while the patient is connected to a drip. As a first step, the patient is administered with 200 ml of NaCl 0.9%. Then an amount of insulin is added such that concentration of glucose in the patient's blood reaches the level of 1.6-3.6 mmol/1.

Subsequently, the following pharmacological compositions are administrated through the patient's injection port: consistently single dose of solution of VINPOCETINE® or CAVINTON®1 ml 5 mg for improving of a cerebral blood flow and rheological properties of a blood.

Next step comprises administering nootropic pharmacological composition groups, such as PIRACETAM® or NOOTROPIL® of 5 ml of 20%, 10 mg of a CORTEXIN® to 10 ml. In the final step, a stimulator of fabric neogenesis solution of 200 mg of ACTOVEGIN®5 ml, is administered to the patient. The optimal regiment prove to a single therapy a week, up to the four sessions overall for a given patient.

The aforementioned procedure has proven to be devoid of any physiological inconvenience for the subject patients. Positive changes are observed by patients on a second day after therapy.

Clinical tests being conducted over five years and involving approximately 25 patients with encephalopathies of various genesis (predominantly, having vascular, posttraumatic and multifactorial genesis) have been observed.

Evaluation of clinical trials and its outcomes was conducted based on the following factors:
nature of patients' complaints;
neurovisual examination of the subject patients;
Examinations were conducted after the 4th session of therapy and repeated in 6 months after the last session.

The received positive results of the treatment were lasted approximately six months following the therapy, with observation of return of some of the prior symptoms. It is to be noted that for the patients who underwent four sessions of therapy, the results of the treatment lasted for approximately 5-7 months.

As examples are provided data from patients' case histories.

Example 1

Patient Saule T., 57 years. Complained to a numbness of the left leg and the left arm, disturbance of the speech, constant headaches as migraine, a sonitus.

Diagnosis: Left-side ischemic stroke, left-side hemiparesis, speech dysfunction. Discirculatory encephalopathy.

Received several courses of standard therapy, physiotherapy and exercises without changes.

The following method of treatment was conducted on the subject patient:
NaCl 0.9%-200 ml is intravenously connected, insulin to the glucose contents of 1.6-3.6 mmol/1 into blood is introduced, then introduction of drugs is begun intravenously in a successive order: solution of VINPOCETINE® of 1 ml 5 mg, further with an interval of 30 seconds solution of PIRACETAM® of 5 ml 20%, then with an interval of 30 seconds solution of CEREBROLYSIN® of 215.2 mg/ml 2 ml, then with an interval of 30 seconds solution of ACTOVEGIN® of 200 mg 5 ml is introduced. The session of therapy on that was complete.

Were carried out four courses of such therapy, once a week each.

On the end of a course neurovisual survey revealed restoration of range of limbs motion, sustainability in Romberg's position, symmetry of tendinous reflexes and a muscular power of limbs.

Subjectively the patient notes appreciable improvement of a condition. The speech, sensitivity and mobility of limbs were completely restored. Headaches ceased completely. Notes risings of level of vigor, ease of processes of storing and procreation of information, decrease of nervousness and concern.

For the preventive purpose six months later repeatedly passed four sessions of therapy.

No negative dynamics signed for four years of observation.

Example 2

Patient Zoya K., 66 years. Complains to a headache, general weakness, giddiness, consciousness disturbance (opacification, syncopes), disturbance of spatial orientation, sleep disorder, memory disturbance.

Diagnosis: A state after the postponed multiple microinsults, an atrophy of a cortex of larger hemispheres, ICA kinking, encephalopathy of 3 St.

Received standard therapy within a year with negative dynamics, that was referred on obtaining disability.

The following method of treatment was conducted on the subject patient:
NaCl 0.9%-200 ml is intravenously connected, insulin to the glucose contents of 1.6-3.6 mmol/1 into blood is introduced, after 15 minutes, then introduction of drugs intravenously by a successive order is begun: solution of CAVINTON®1 ml 5 mg is introduced, further with an interval of 30 seconds—solution of NOOTROPIL®5 ml 20%, with an interval of 30 seconds solution of CORTEXIN® 0 mg is introduced, then with an interval of 30 seconds solution of ACTOVEGIN®200 mg 5 ml is introduced. The session of therapy on that was complete.

Therapy was carried out once a week. Total amount of therapies—four.

On the end of a course were restored functions of a vestibular mechanism, registered sustainability in Romberg's test, ease in orientation in space appeared. Normalization of cognitive functions of a brain and vigor was noted. Coordination was completely restored, the depression and headaches ceased. Notes ease of processes of storing and procreation of information. Working capacity was completely restored.

Patient subjectively observed significant improvement of a condition. The dream, memory, appetite were restored.

With the preventive purpose six months later repeatedly took place four sessions of therapy.

Absence of negative dynamic in 4 years.

Example 3

Patient Vera Z., 80 years. Complaints are to the general weakness, dyspnea, strong giddiness, sonitus, equilibrium disturbance, sleep disorder, memory impairment, and depressive mood.

Diagnosis: Vertebrobasilar insufficiency, discirculatory encephalopathy of 2 St.

Received standard therapy within the last 15 years, physical condition with negative dynamics.

The following method of treatment was conducted on the subject patient:

NaCl 0.9%-200 ml is intravenously connected, insulin to the glucose contents of 1.6-3.6 mmol/1 into blood is introduced, then introduction of drugs intravenously by a successive order is begun: solution of VINPOCETINE® 1 ml 5 mg is introduced, further with an interval of 30 seconds—solution of NOOTROPIL® 5 ml 20%, with an interval of 30 seconds solution of CORTEXIN® 10 mg is introduced, then with an interval of 30 seconds solution of ACTOVEGIN® 200 mg 5 ml is introduced. The session of therapy on that was complete.

Therapy took place once a week for four times.

On the end of a course restored functions of a vestibular mechanism, was observed sustainability in Romberg's position, ease in the movements appeared. Cognitive functions of a brain improved. The dyspnea virtually disappeared. The level of vigor objectively raised. Subjectively were noted definite improvements of a physical condition. Giddiness went gone. The dyspnea considerably decreased, the depression passed. Patient ceased to notice a sonitus.

With the preventive purpose six months later, repeatedly patient undertook four sessions of therapy. For the last two years after therapy no negative dynamics were observed.

Example 4

Patient Svetlana L., 50 years.

Complaints are to the general weakness, strong giddiness, equilibrium disturbance, sleep disorder, memory impairment, depressive mood.

Diagnosis: Cerebral cavernoma, tetra paresis, motor aphasia, dysfunction of pelvic organs, vestibular syndrome, encephalopathy.

Patient undertook standard therapy within the last two years. Improvements in a condition were noted, while vestibular syndrome and cognitive disturbances remained. The following method of treatment was conducted on the subject patient: NaCl 0.9%-200 ml is intravenously connected, insulin to the glucose contents of 1.6-3.6 mmol/1 into blood is introduced, then introduction of drugs intravenously by a successive order is begun: solution of CAVINTON® 1 ml 5 mg is introduced, further with an interval of 30 seconds—solution of PIRACETAM® 5 ml 20%, then with an interval of 30 seconds solution of CORTEXIN® 10 mg is introduced, then with an interval of 30 seconds solution of ACTOVEGIN® 200 mg 5 ml is introduced. The session of therapy on that was complete.

Therapy was carried out once a week. Total amount of therapies 4.

On the end of a course there are noted restoration of functions of a vestibular mechanism, recovery of the speech, the depressive syndrome, fatigability was stopped. Control over function of pelvic organs was restored. Also improvement of cognitive functions of a brain and rising of level of vigor were marked.

Subjectively, patient notes significant improvement of mood and the general condition, began to control a bladder. Giddiness stopped, the depression ceased.

With the preventive purpose 9 months later, repeatedly patient undertook 4 sessions of therapy.

For the last 2 years after therapy, no negative dynamics noted.

Example 5

Patient Karen V., 67 years old. Complaints to weakness, fast fatigue, pains in heart, unsteady gait, frequent headaches, impaired concentration, increased arterial blood pressure, entotic sound.

Diagnosis: Hypertension of the 2nd degree, Discirculatory encephalopathy.

The following method of treatment was conducted on the subject patient:

NaCl 0.9%-200 ml is intravenously connected, insulin to the glucose contents of 1.6-3.6 mmol/1 into blood is introduced, then introduction of drugs intravenously by a successive order is begun: solution of TRENTAL® 20 mg/ml 5 mg is introduced, further with an interval of 30 seconds solution of CERAXON® 500 mg-4 ml, then with an interval of 30 seconds solution of CEREBROLYSIN® 215.2 mg/ml-2 ml is introduced, then with an interval of 30 seconds solution of ACTOVEGIN® 200 mg 5 ml is introduced.

One such therapy per week is carried out. Total number of therapies 4.

At the end of course during the neuro-visual examination stability in Romberg's pose, symmetry of tendinous reflexes and muscular force of extremities, normalization of arterial tension to the level of 120/80 mm Hg is noticed.

The patient subjectively notices a considerable improvement of state. Pains in heart ceased to disturb. Increase of vivacity, activity. Presence of ease and joy feeling. Headaches were stopped. He notices increase of energy level, ease of reminding processes and reproduction of information. Reduction of nervousness and anxiety.

Within 3 years of follow-up no negative dynamics.

Example 6

Patient Raymond, 60 years old. Complaints to the tired state, frequent colds, weakness, sleep disorder, temper tantrum, memory and concentration impairment. Apathy.

Diagnosis: Encephalopathy of the mixed genesis.

The following method of treatment was conducted on the subject patient:

NaCl 0.9%-200 ml is intravenously connected, insulin to the glucose contents of 1.6-3.6 mmol/1 into blood is introduced, after 15 minutes, then introduction of drugs intravenously by a successive order is begun: solution of PENTOXIFYLLINE® 20 mg/ml 5 mg is introduced, further with an interval of 30 seconds—solution of MEXIDOL® 5% 2 ml, then with an interval of 30 seconds solution of CEREBROLYSIN® 215.2 mg/ml-2 ml is introduced, then with an interval of 30 seconds solution of SOLCOSERYL® 42.5 mg/ml 2 ml is introduced. At that the session of therapy was completed.

One such therapy per week is carried out. Total number of therapies 4.

Example 7

Marina Z., 58 years old. Complaints to headaches, memory and attention impairment, seeing spots, periodically deterioration in coordination when walking and impairment in writing.

Diagnosis: Discirculatory encephalopathy of the 2nd degree, destruction of a vitreous humor. She repeatedly received a standard therapy under this diagnosis. The gradual deterioration in dynamics.

The following method of treatment was conducted on the subject patient:

NaCl 0.9%-200 ml is intravenously connected, insulin to the glucose contents of 1.6-3.6 mmol/1 into blood is introduced, then introduction of drugs intravenously by a successive order is begun: solution of CAVINTON®1 ml-5 mg is introduced, further with an interval of 30 seconds—solution of CERAXON®500 mg-4 ml, then with an interval of 30 seconds solution of CORTEXIN®10 mg is introduced, then with an interval of 30 seconds solution of SOLCOS-ERYL® 42.5 mg/ml-2 ml is introduced.

One such therapy per week is carried out. Total number of therapies-4.

At the end of the course the stability in Romberg's pose is noticed, ease and clearness appeared when writing. Improvement of cognitive functions of a brain. Increase of energy level. She subjectively notices an obvious improvement of state, seeing spots completely disappeared.

Within the last 2 years after therapy—no negative dynamics. Two years later one seeing spot appeared (there were five).

Example 8

Marat R., 80 years old. He does not show complaints. He is apathetic. He comes into contact hardly. Objectively—the right-sided central hemiparesis, urinary incontinence, emotional meanness, hypodynamia, hypomimia. From the Anamnesis in 2008 he had an ischemic stroke, in half a year one more. Within 7 years he was treated in Israel, Korea, Europe and Kazakhstan. The last 3 years—no obvious improvements.

Diagnosis: The state after the suffered ischemic strokes in 2008, the right-sided central hemiparesis, discirculatory encephalopathy of the 3rd degree.

He received a standard therapy within the last 7 years. The last 3 years—the state with no improvements.

The following method of treatment was conducted on the subject patient:

NaCl 0.9%-200 ml is intravenously connected, insulin to the glucose contents of 1.6-3.6 mmol/1 into blood is introduced, then introduction of drugs intravenously by a successive order is begun: solution of TRENTAL®20 mg/ml-5 ml is introduced, further with an interval of 30 seconds—solution of NOOTROPIL® 5 ml 20%, then with an interval of 30 seconds solution of CORTEXIN®10 mg is introduced, then with an interval of 30 seconds solution of SOLCOS-ERYL®42.5 mg/ml 2 ml is introduced.

One such therapy per week is carried out. Total number of therapies-4.

Since the 3-rd week he began to control urination, there was an emotional answer to surrounding events, he began to communicate actively with staff of clinic, the gait gained dynamism, and he began to smile and joke.

At the end of course the restoration of vestibular apparatus functions, recovery of the speech and cognitive functions of the brain is noticed. Control over pelvic organs function was completely restored.

He subjectively notices a considerable improvement of memory, mood, and the general state. He began to control a bladder. The patient became socially minded.

Within the last 3 years after therapy no negative dynamics.

Example 9

Patient B-ov B., 68 years old. Complaints to apathy up to the depression, loss of interest in life, work, family, the general total fatigue, emotional emptiness. Sleep disorder, memory impairment.

Diagnosis: Hypertension of the 1st degree, discirculatory encephalopathy of the 2nd degree.

The following method of treatment was conducted on the subject patient:

NaCl 0.9%-200 ml is intravenously connected, insulin to the glucose contents of 1.6-3.6 mmol/1 into blood is introduced, then introduction of drugs intravenously by a successive order is begun: solution of TRENTAL®20 mg/ml 5 ml is introduced, further with an interval of 30 seconds—solution of MEXIDOL® 5%-2 ml, then with an interval of 30 seconds solution of CORTEXIN®10 mg is introduced, then with an interval of 30 seconds solution of SOLCOS-ERYL®42.5 mg/ml 2 ml is introduced.

At the end of course the restoration of cognitive functions, mood, and activities is noticed. The apathy and depression were completely gone. There were energy level and creativity, the sleep was restored. He returned to the senior management position.

Within the last 2 years after therapy no negative dynamics.

The foregoing description of the preferred embodiment of the invention has been presented for purposes of illustration and description. It is not intended to be exhaustive or to limit the invention to the precise form disclosed. Many alternatives, modifications, and variations will be apparent to those skilled in the art in light of the above teaching.

Any pharmacological composition and formulae are conceptual illustrations allowing for an explanation of the present invention. Notably, the pharmacological composition and formulae and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein.

Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein.

It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments but should be defined only in accordance with the following claims and their equivalents.

The invention claimed is:

1. A method of treatment of encephalopathy in a patient in need thereof, the method comprising
    administering insulin intravenously to a patient, thereby decreasing concentration of glucose in the patient's blood to 1.6-3.6 mmol per liter of blood;
    consecutively administering the patient with single doses of a plurality of pharmacological solutions with nootropic action, thereby treating encephalopathy in the patient.

2. The method of claim 1, wherein the step of administering the patient with single doses of the plurality of pharmacological solutions with nootropic action comprises administering the patient with single doses of each the plurality of pharmacological solutions with a thirty-second interval.

3. The method of claim 1, wherein a first-pharmacological solution administered to the patient comprises a vascular medicine with pharmacological effect.

4. The method of claim 3, wherein the vascular medicine is a pharmacological solution of vinpocetin.

5. The method of claim 3, wherein the vascular medicine is a pharmacological solution of pentoxifyllin.

6. The method of claim 1, wherein a second-pharmacological solution administered to the patient is a direct nootropic effected pharmacological composition.

7. The method of claim 6, wherein the direct nootropic effected pharmacological composition is a pharmacological composition of 2-oxo-1-pyrrolidine acetamide.

8. The method of claim 6, wherein the direct nootropic effected pharmacological composition is a pharmacological composition of Ethylmethylhydroxypyridine succinate (Mexidol).

9. The method of claim 6, wherein the direct nootropic effected pharmacological composition is a pharmacological composition of Citicoline sodium.

10. The method of claim 1, wherein a third-pharmacological solution administered to the patient is a peptide pharmacological composition.

11. The method of claim 10, wherein the peptide pharmacological composition is a pharmacological composition of Polypeptides of the cerebral cortex of cattle (Cortexin).

12. The method of claim 10, wherein the peptide pharmacological composition is a pharmacological composition of Polypeptides of the cerebral of pigs (Cerebrolysin).

13. The method of claim 1, wherein a fourth pharmacological solution administered to the patient is a metabolic pharmacological composition.

14. The method of claim 1, wherein metabolic pharmacological composition comprises at least one of a pharmacological composition of deproteinized calf blood haemoderivative (Actovegin) and a pharmacological composition of deproteinized calf blood extract (Solcoseryl).

15. The method of claim 1, wherein the method procedures of administering of the aforementioned pharmacological compositions are carried out once a week, in total of four administering sessions.

* * * * *